US010335326B2

United States Patent
Wu

(10) Patent No.: US 10,335,326 B2
(45) Date of Patent: *Jul. 2, 2019

(54) SMART NURSING CONSUMABLE AND PHYSIOLOGICAL MONITORING DEVICE USING THE SAME

(71) Applicant: Sinopulsar Technology Inc., Hsinchu (TW)

(72) Inventor: Tien-Hsiang Wu, Hsinchu (TW)

(73) Assignee: Sinopulsar Technology Inc., Hsinchu (TW)

( * ) Notice: Subject to any disclaimer, the term of this patent is extended or adjusted under 35 U.S.C. 154(b) by 219 days.

This patent is subject to a terminal disclaimer.

(21) Appl. No.: 15/197,773

(22) Filed: Jun. 30, 2016

(65) Prior Publication Data

US 2017/0071803 A1  Mar. 16, 2017

(30) Foreign Application Priority Data

Sep. 15, 2015  (CN) .......................... 2015 1 0584825

(51) Int. Cl.
| A61F 13/15 | (2006.01) |
| --- | --- |
| A61F 13/20 | (2006.01) |
| A61F 13/84 | (2006.01) |
| A61B 5/00 | (2006.01) |
| A61F 13/00 | (2006.01) |
| A61B 5/0205 | (2006.01) |
| A61B 5/01 | (2006.01) |
| A61F 13/42 | (2006.01) |
| A61B 5/024 | (2006.01) |
| A61B 5/08 | (2006.01) |
| A61B 5/0245 | (2006.01) |
| A61B 5/053 | (2006.01) |

(52) U.S. Cl.
CPC ............ *A61F 13/84* (2013.01); *A61B 5/0022* (2013.01); *A61B 5/01* (2013.01); *A61B 5/0205* (2013.01); *A61B 5/6808* (2013.01); *A61B 5/74* (2013.01); *A61F 13/00004* (2013.01); *A61F 13/42* (2013.01); *A61B 5/0245* (2013.01); *A61B 5/02438* (2013.01); *A61B 5/0531* (2013.01); *A61B 5/0816* (2013.01); *A61B 2562/0219* (2013.01); *A61B 2562/0271* (2013.01); *A61F 2013/424* (2013.01); *A61F 2013/8473* (2013.01)

(58) Field of Classification Search
CPC .... A61F 13/42; A61F 13/15; A61F 13/15699; A61F 13/2051; A61F 2013/8491; G01N 27/225
USPC ........... 604/361; 156/285; 242/520; 493/343
See application file for complete search history.

(56) References Cited

U.S. PATENT DOCUMENTS

| 2004/0147888 | A1* | 7/2004 | Huang | ..................... | A61F 13/42 |
| | | | | | 604/361 |
| 2014/0296808 | A1* | 10/2014 | Curran | .................... | A61F 13/42 |
| | | | | | 604/361 |
| 2014/0350503 | A1* | 11/2014 | Bosaeus | .................. | A61F 13/42 |
| | | | | | 604/361 |
| 2017/0071797 | A1* | 3/2017 | Wu | .......................... | A61F 13/42 |

* cited by examiner

*Primary Examiner* — Jon Eric C Morales

(57) ABSTRACT

A smart nursing consumable includes an absorbent body and a sensor module. The absorbent body includes a water-absorbing layer. The sensor module is disposed above the water-absorbing layer and includes a plurality of wires. A physiological monitoring device employing the aforementioned smart nursing consumable is also provided.

13 Claims, 4 Drawing Sheets

SMART NURSING CONSUMABLE AND PHYSIOLOGICAL MONITORING DEVICE USING THE SAME

TECHNICAL FIELD OF THE INVENTION

The present invention relates to a nursing consumable, and more particularly to a smart nursing consumable and a physiological monitoring device employing the smart nursing consumable.

BACKGROUND OF THE INVENTION

Conventionally, nursing consumables such as gauze, urinary pad, diaper, replacement sheets etc., has no sensing functions, and therefore cannot notify the active conditions of the nursing consumables or notify the care receivers as well as the caregivers to change the nursing consumables when become dirty. In addition, the conventional nursing consumables do not have physiological sensing functions, either. In generally, some care receivers such as infants, elderly with dementia or patients with limited mobility, may not be able to self-control their excretions. Therefore, it is common among care receivers to wear diapers to lessen the burden of the caregivers.

However, moisture in diaper, PH of urine, and proteins or bacteria in feces tend to cause skin-related infections among diapered care receivers. Therefore, it is quite important for caregivers to determine whether diapers are dirty and when to change dirty diapers, as well as to predict when the care receivers might urinate or excrete. Conventionally, the determination of timing to change diapers is realized based on caregivers actively and physically touching the diaper, thereby sensing whether the humidity inside the diaper is too high. Alternatively, caregivers would passively wait until the care receivers express discomfort. However, the aforementioned judgments depend primarily on personal experiences or feelings of the caregivers, and the caregivers may judge incorrectly when the care receivers give uncertain expressions.

As a result, smart diapers capable of sensing the presence of excretions have been developed. Generally, a conventional smart diaper has a conductive tape formed by printing conductive resins on a waterproof layer of the smart diaper. The conductive tape is covered with a water-absorbing layer, and a transceiver assembly is used to sense the impedance changes of the conductive tape. When the water-absorbing layer absorbs certain amount of urine, some of the urine may permeate to the conductive tape and consequently the conductive tape has an impedance change. Therefore, once the transceiver assembly senses that the impedance of the conductive tape has changed, it would notify that the water-absorbing layer has absorbed certain amount of urine and it is time to change a new smart diaper.

Conventionally, the waterproof layer is made smooth so that the conductive resins can be printed thereon and the connection between the waterproof layer and the transceiver assembly can be realized more easily. However, because feces could not permeate to the conductive tape through the water-absorbing layer, the conductive tape would not have an impedance change even when the care receiver has excreted. Therefore, the determination of diaper change for the care receiver still relies on the caregiver's attention. Moreover, convention smart diapers can only notify the caregivers when to change but not sense or analyze each urination of the care receivers.

SUMMARY OF THE INVENTION

One objective of the present invention is to provide a smart nursing consumable for sensing and collecting excrement and physiological information of the care receivers.

Another objective of the present invention is to provide a physiological monitoring device for monitoring a health condition of the care receivers.

The present invention provides a smart nursing consumable, which includes an absorbent body and a sensor module. The absorbent body includes a water-absorbing layer. The sensor module is disposed above the water-absorbing layer and includes a plurality of wires.

In one embodiment, the absorbent body further includes a water draining layer. The water draining layer is disposed above the water-absorbing layer. The sensor module is disposed on the water draining layer. The sensor module further includes a first porous sheet, a second porous sheet and a conductive pad. The wires are disposed between the first porous sheet and the second porous sheet. The first porous sheet is disposed adjacent to the water-absorbing layer. The conductive pad is connected to the wires through pores of the second porous sheet.

In one embodiment, a material of the conductive pad is selected from at least one element in a group consisting of conductive plastic gum, conductive gel, conductive plastic, conductive ink, conductive paint and carbon film.

In one embodiment, the smart nursing consumable includes smart nursing pants, a smart diaper, a smart nursing pad, a smart sanitary napkin or smart gauze.

The present invention also provides a physiological monitoring device, which includes the aforementioned smart nursing consumable, a transceiver assembly and a monitoring module. The transceiver assembly is removably coupled to the smart nursing consumable. The transceiver assembly includes an impedance sensor and a signal processing module. The impedance sensor is electrically connected to the wires and configured to sense an impedance value between the wires so as to obtain a plurality of time-dependent impedance values and a time-dependent impedance change. The signal processing module is electrically connected to the impedance sensor and configured to convert the time-dependent impedance value and the time-dependent impedance change sensed by the impedance sensor into a notification signal, wherein the notification signal indicates active conditions of the smart nursing consumable. The monitoring module is configured to receive the notification signal provided by the transceiver assembly.

In one embodiment, the transceiver assembly further includes a physiological signal sensor. The physiological signal sensor is electrically connected to the signal processing module and configured to sense a physiological signal of a care receiver.

In one embodiment, the physiological signal sensor includes an acceleration sensor. The acceleration sensor is disposed close to the smart nursing consumable and configured to sense at least one of a heart rate and a respiration rate of the care receiver.

In one embodiment, the physiological signal sensor includes a thermal resistor. The thermal resistor is disposed close to the smart nursing consumable and configured to sense a skin temperature of the—care receiver.

In one embodiment, the physiological signal sensor includes a bioelectric sensor. The bioelectric sensor is disposed close to the smart nursing consumable and configured to sense a heart rate of the care receiver.

In one embodiment, the absorbent body has a diaper shape. The transceiver assembly further includes a clamp body, and the clamp body is configured to clamp a belt of the absorbent body.

In one embodiment, the transceiver assembly further includes a wireless signal transmitter. The wireless signal transmitter is electrically connected to the signal processing module and configured to transmit the notification signal.

In one embodiment, the monitoring module includes a reminder element.

In one embodiment, the monitoring module includes a monitoring data transfer element.

In one embodiment, the skin temperature increases with a severity of a wound infection of the care receiver.

In the smart nursing consumable according to the embodiments of the present invention, because the sensor module is disposed above the absorbent body, urination or excretion of the care receiver can be detected and determined according to the sensed signal, thereby facilitating the determination of the care receiver's conditions. Further, because the aforementioned smart nursing consumable is employed, the physiological monitoring device of the present invention can further analyze and predict the excretions and the physiological conditions of the care receiver.

BRIEF DESCRIPTION OF THE DRAWINGS

The present disclosure will become more readily apparent to those ordinarily skilled in the art after reviewing the following detailed description and accompanying drawings, in which.

DETAILED DESCRIPTION OF PREFERRED EMBODIMENTS

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

The present invention provides a smart nursing consumable for a care receiver and for detecting important physiological signals therefrom and collecting excretions (such as urine, feces, etc.) or other body fluids (such as sweat or blood, etc.) of the care receiver. The smart nursing consumable of the present invention may be implemented as smart nursing pants, smart diapers, smart nursing pads, smart sanitary napkins for menstruation or smart gauze for covering wounds; and the present invention is not limited thereto. In addition, the smart nursing consumable of the present invention may be further implemented as mats or packaging materials for collecting excretions of the care receiver. The smart nursing consumable of the present invention will be exemplarily implemented as a smart nursing diaper, and the structures and functions thereof will be described in detail as follow.

Figure 1:
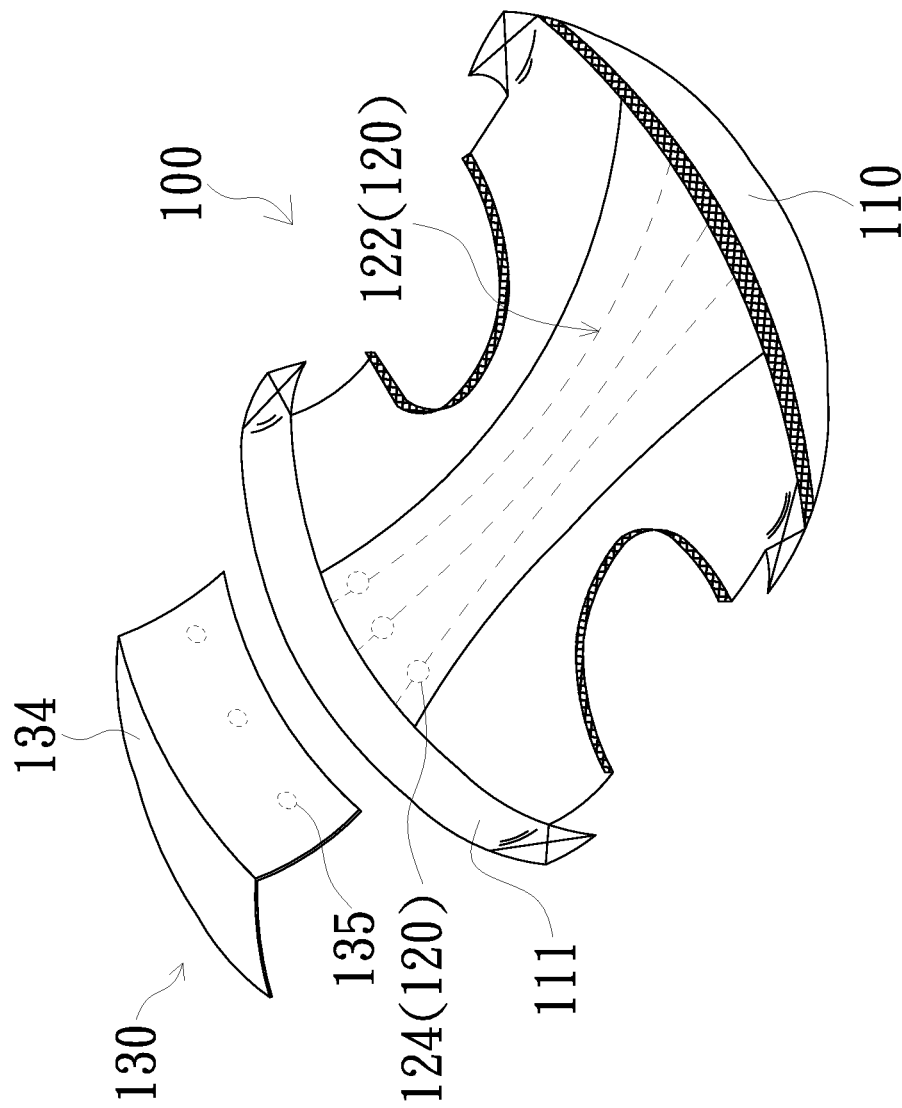
FIG. 1 is a perspective schematic view of a smart nursing consumable and a transceiver assembly in accordance with an embodiment of the present invention.
Figure 2:
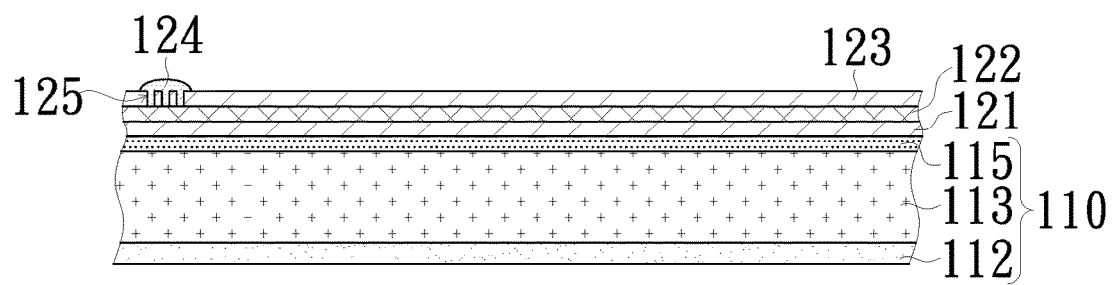
FIG. 2 is a cross-sectional schematic view of a smart nursing consumable in accordance with an embodiment of the present invention.

FIG. 1 is a perspective schematic view of a smart nursing consumable and a transceiver assembly in accordance with an embodiment of the present invention. FIG. 2 is a cross-sectional schematic view of the smart nursing consumable in accordance with the embodiment of the present invention. Please refer to FIG. 1 and FIG. 2. In the present embodiment, the smart nursing consumable 100 can be coupled to the transceiver assembly 130, and the transceiver assembly 130 is reusable. The smart nursing consumable 100 includes an absorbent body 110 and a sensor module 120. The absorbent body 110 includes a waterproof layer 112 and a water-absorbing layer 113 disposed on the waterproof layer 112. The sensor module 120 is disposed above the water-absorbing layer 113. The sensor module 120 includes a plurality of wires 122. The transceiver assembly 130 is removably coupled to the absorbent body 110.

In the present embodiment as shown in FIG. 1 and FIG. 2, the sensor module 120 may further include a conductive pad 124 connected to the wires 122, thereby facilitating the electrical connection between the sensor module 120 and the transceiver assembly 130. Specifically, the absorbent body 110 has a diaper-like shape. The transceiver assembly 130 may further include a clamp body 134 configured to clamp a belt 111 of the absorbent body 110. The clamp body 134 may be a flexible circuit board or a rigid circuit board, and the present invention is not limited thereto. In addition, the absorption body 110 may further include a water draining layer 115. The water draining layer 115 is disposed above the water-absorbing layer 113, and the sensor module 120 is disposed on the water draining layer 115. The sensor module 120 may further include a first porous sheet 121 and a second porous sheet 123. The wires 122 are disposed between the first porous sheet 121 and the second porous sheet 123, and the first porous sheet 121 is disposed adjacent to the water-absorbing layer 113. To facilitate water permeation, both of the first porous sheet 121 and the second porous sheet 123 may be formed with a plurality of evenly-distributed pores. The first porous sheet 121 and the second porous sheet 123 may be non-woven fabric or other porous non-absorbing materials, such as gauze fabric, and the present invention is not limited thereto. The conductive pad 124 may be disposed on the second porous sheet 123 and connected to the wires 122 through the pores of the second porous sheet 123 (only three pores 125 are exemplarily shown in FIG. 2), thereby facilitating the electrical connection between the conductive pad 124 and the wires 122. The first porous sheet 121 and the second porous sheet 123 contribute to moisture isolation. The water draining layer 115 contributes to liquid drainage, so that liquids can be quickly and efficiently drained to the water-absorbing layer 113. In addition, the sensor module 120 in the present embodiment as shown in FIG. 1 is exemplified by including three wires 122; however, the quantity of the wires 122 is not limited in the present invention. In other words, the sensor module 120 may include two wires 122 or more than three wires 122 in another embodiment. It is to be understood that the sensing area of the sensor module 120 increases with the quantity of the wires 122. The wires 122 may metal wires or metal films. The material of the conductive pad 124 may be conductive plastic gum, conductive gel, conductive plastic, conductive ink, conductive paint or other liquid conductive material. In one embodiment, the material of the conductive pad 124 is carbon film. In addition, it is to be understood that the conductive pad 124 may contain two or more of the aforementioned materials.

Figure 3:
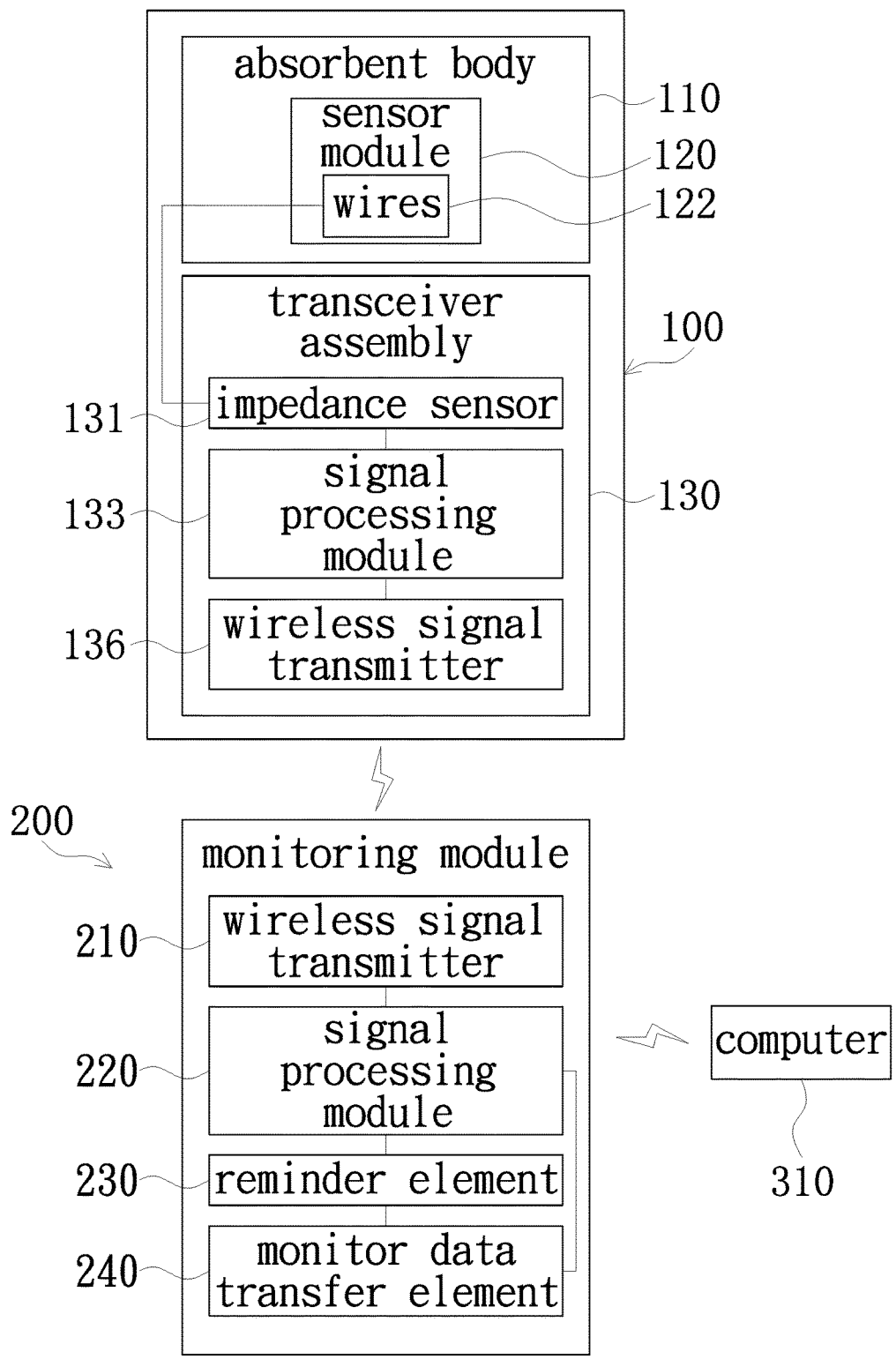
FIG. 3 is a block diagram of a physiological monitoring device in accordance with an embodiment of the present invention.

FIG. 3 is a block diagram of a physiological monitoring device in accordance with an embodiment of the present invention. As shown in FIG. 3, the physiological monitoring device of the present embodiment includes a monitoring module 200, the above-described transceiver assembly 130 and the above-described smart nursing consumable 100. The transceiver assembly 130 of the present embodiment may further include an impedance sensor 131 and a signal processing module 133. The impedance sensor 131 is electrically connected to the wires 122 of the smart nursing consumable 100 and is configured to sense the impedance value between the wires 122 so as to obtain a plurality of time-dependent impedance values and a time-dependent waveform-like impedance change. The signal processing module 133 is electrically connected to the impedance sensor 131. The signal processing module 133 is configured to store and convert the time-dependent impedance values and the time-dependent impedance change sensed by the impedance sensor 131 into a notification signal, which indicates active conditions of the smart nursing consumable 100. Namely, according to the notification signal, the active conditions (such as the level of liquid absorption, and whether changing the smart nursing consumable 100 has become necessary, etc.) of the smart nursing consumable 100 can be analyzed. In the present embodiment, the transceiver assembly 130 may further include a wireless signal transmitter 136. The wireless signal transmitter 136 is electrically connected to the signal processing module 133 and configured to transmit the notification signal and stored data.

The impedance sensor 131 and the signal processing module 133 may be disposed in the clamp body 134 (shown in FIG. 1) and electrically connected with each other through the circuit of the clamp body 134. The clamp body 134 in FIG. 1 may further include a connecting member 135. The connecting member 135 is connected to the conductive pad 124, thereby facilitating the electrical connection between the impedance sensor 131 and the wires 122. In the present embodiment, when urine or feces permeate to the wires 122, the impedance value between the wires 122 changes accordingly, and the impedance sensor 131 is used to sense the changes in the impedance value.

The wires 122 are disposed above the water-absorbing layer 113. Therefore, in each urination, the urine would sequentially pass through the second porous sheet 123, the wires 122, the first porous sheet 121, and eventually be absorbed by the water-absorbing layer 113. When the urine permeates to the wires 122, the impedance value between the wires 122 would exhibit a significant change; then, the impedance change is narrowed when the urine permeated to the wires 122 is gradually absorbed by the water-absorbing layer 113; and eventually the impedance between the wires 122 returns to the original value when the urine is completely absorbed by the water-absorbing layer 113. As a result, in every urination the impedance sensor 131 can sense a time-dependent waveform-like impedance change. Through the waveform-like impedance change, the time and duration of each urination are recorded and analyzed; and consequently, the number of times and frequency of urination, as well as the amount of urine, etc. are obtained. As a result, detection, determination and prediction of the health condition of the care receiver, such as urination frequency or urinary tract infections, are facilitated. In addition, when the care receiver excretes, the feces would pass through the pores of the second porous sheet 123 and stick to the wires 122 or the areas between the wires 122; and therefore, the impedance value changed due to the excrements would not return back to the original value. As a result, every time an unrecoverable impedance is observed, excretion of the care receiver can be determined. Further, according to the quantity of the wires 122 having short circuit, areas of the smart nursing consumable 100 wetted by urine or other liquids can be determined. Further, the smart nursing consumable 100 of the present invention may be implemented with specific technical features to measure reactance or resistance by frequency or to analyze PH values, thereby facilitating the sensing and determination of the care receiver's physiological conditions. Therefore, it is to be understood that the present invention is different from the prior art, in which only the threshold value of resistance is measured.

In the smart nursing consumable 100 of the present embodiment, because the sensor module 120 is disposed above the absorbent body 110, the urination or excretion of the care receiver can be detected and determined according to the waveform of the sensed signal, thereby facilitating the determination and prediction of the care receiver's conditions. In addition, to provide comfort without any foreign body sensation and to prevent the sensor module 120 from blocking liquid permeation, the present invention employs the wires 122 instead of the conductive tapes used in the prior art. In a preferred embodiment, the width of the wire 122 ranges from 0.05 millimeter (mm) to 1 mm. Having such widths, the wires 122 tend to fall into the pores of the first porous sheet 121 and the second porous sheet 123, leading to poor connection between the wires 122 and the connecting member 135 of the clamp body 134; therefore, the conductive pad 124 is employed to avoid the occurrence of the aforementioned situation and the resulted error signal. In addition, by using the first porous sheet 121 and the second porous sheet 123 to wrap around the wires 122, the wires 122 are prevented from direct contact with the care receiver's skin and the water draining layer 115, thus avoiding the error signal. In addition, the wire 122 may be made of alloy to avoid wire breakage. In one embodiment, the wire 122 is made of tin-copper alloy, but the present invention is not limited thereto.

When applied to smart gauze for covering wounds, the smart nursing consumable 100 of the present invention may be used to sense and analyze whether the wound is bleeding and whether the bleeding is excessive and to measure the care receiver's skin temperature to determine whether an inflammation is present. The monitoring module 200 is configured to receive the notification signal provided by the transceiver assembly 130. The monitoring module 200 may include a wireless signal transmitter 210 and a signal processing module 220 that are electrically connected with each other. In the present embodiment, the signal processing module 133 of the transceiver assembly 130 converts the impedance values between the wires 122 and the time-dependent impedance change sensed by the impedance sensor 131 into the notification signal. The wireless signal transmitter 136 of the transceiver assembly 130 then transmits the notification signal to the monitoring module 200. The monitoring module 200 receives the notification signal through the wireless signal transmitter 210 thereof. Finally, the signal processing module 220 of the monitoring module 200 analyzes the notification signal, such as analyzing the time-dependent impedance values and changes sensed by the impedance sensor 131, to determine the physiological behaviors (such as urination, excretion or sweating) of the care receiver.

In addition, the monitoring module 200 may further include a reminder element 230. The reminder element 230 is configured to issue a timely alarm, such as that for reminding the caregivers to change the smart nursing consumable 100, in accordance with a received sensing result outputted from the signal processing module 220 according to the notification signal. In the present embodiment, because the transceiver assembly 130 is removably coupled to the smart nursing consumable 100, the transceiver assembly 130 can be recoupled to a new smart nursing consumable 100 from a dirty smart nursing consumable 100, consequently lowering the cost of nursing care and avoiding waste of valuable resources. Specifically, the reminder element 230 is electrically connected to the signal processing module 220, and the signal processing module 220 may control the reminder element 230 to issue an alarm timely in accordance with the sensing results. In one embodiment, the reminder element 230 is an acoustic warning device or an optical warning device configured to issue alarms by whistling or flashing lights, respectively. It is to be understood that the type and quantity of the reminder element 230 is not limited in the present invention.

In one embodiment, analysis of the time-dependent impedance values and changes sensed by the impedance sensor 131 is performed by the monitoring module 200. In another embodiment, the analysis of the time-dependent impedance change may be performed by the signal processing module 133 and the analysis result is then converted into the notification signal. Further, in another embodiment, the monitoring module 200 and the transceiver assembly 130 can communicate with each other via wired connection, instead of using the wireless signal transmitters 136 and 210.

In addition, the monitoring module 200 of the present embodiment may further include a monitoring data transfer element 240. The monitoring data transfer element 240 is configured to transfer the obtained monitoring data and warning signals to the caregiver's computer 310 or other portable electronic devices, such as smart mobile phones, tablets or smart watches, thereby providing instant reminders to the caregiver. In another embodiment, the monitoring data transfer element 240 may be integrated into the wireless signal transmitter 210.

Figure 4:
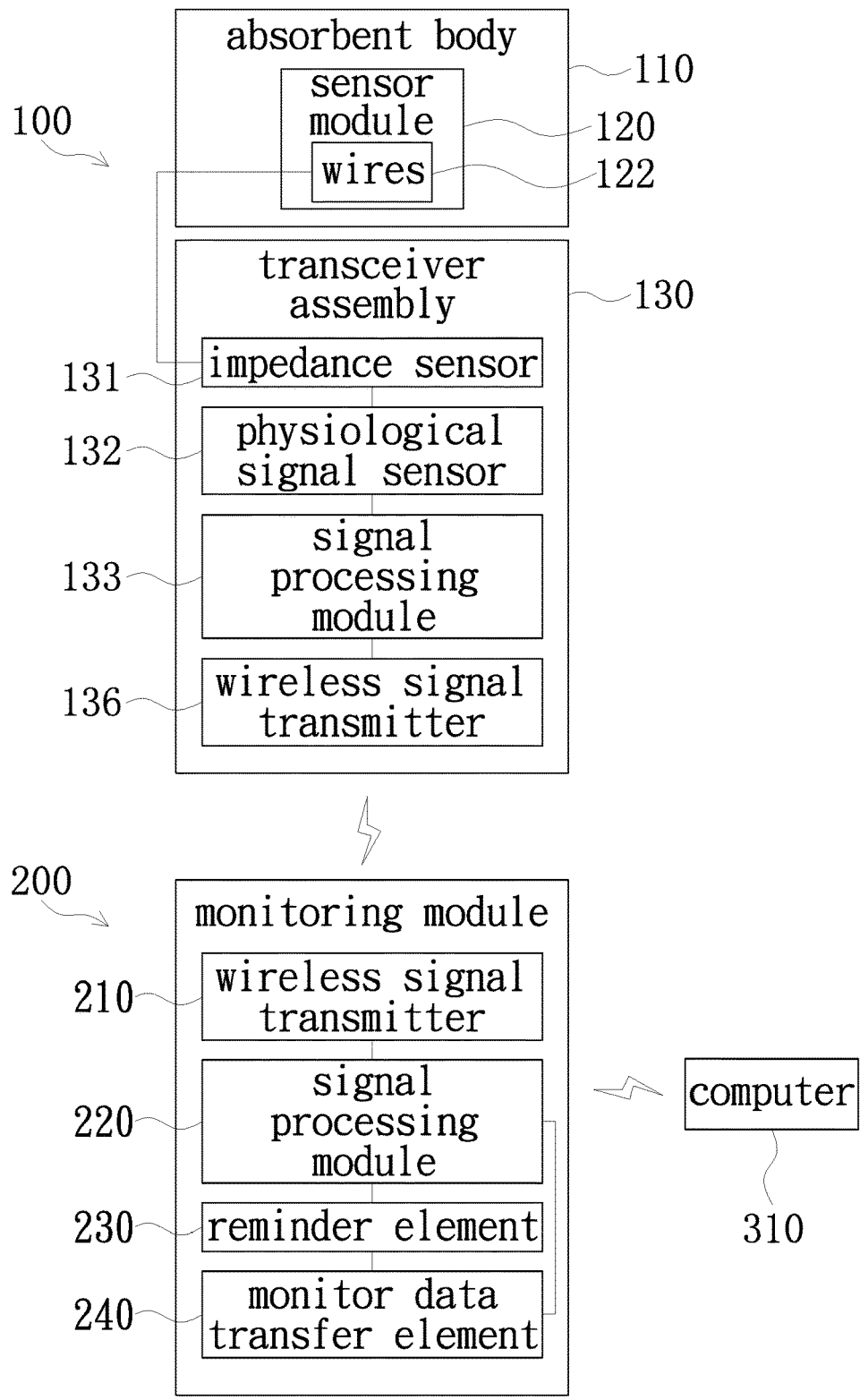
FIG. 4 is a block diagram of a physiological monitoring device in accordance with another embodiment of the present invention.

FIG. 4 is a block diagram of a physiological monitoring device in accordance with another embodiment of the present invention. As shown in FIG. 4, the physiological monitoring device of the present embodiment is similar to the physiological monitoring device of FIG. 3. A difference lies in that the transceiver assembly 130a of the present embodiment further includes a physiological signal sensor 132. The physiological signal sensor 132 is electrically connected to the signal processing module 133 and configured to sense physiological signals, such as heart rate, respiration rate and skin temperature, of the care receiver. In general, the care receiver's physiological conditions can be monitored through the heart rate, the respiration rate or the skin temperature of the care receiver. For example, if a wound infection of the care receiver is getting severe, the sensed skin temperature of the care receiver would increase. The physiological signal sensor 132 may include one sensor or a plurality of sensors with different sensing capabilities. In one embodiment, the physiological signal sensor 132 is an acceleration sensor, which is disposed close to the smart nursing consumable 100 and configured to sense the heart rate and/or respiration rate of the care receiver. In other words, the physiological signal sensor 132 may sense the heart rate or the respiration rate of the care receiver; or, the physiological signal sensor 132 may sense the heart rate and the respiration rate of the care receiver simultaneously. The aforementioned acceleration sensor may be a single-axial acceleration sensor, a dual-axial acceleration sensor, or a tri-axial acceleration sensor. In another embodiment, the physiological signal sensor 132 is a thermal resistor, which is disposed close to the smart nursing consumable 100 and configured to sense the skin temperature of the care receiver. In still another embodiment, the physiological signal sensor 132 is a bioelectric sensor, which is disposed close to the smart nursing consumable 100 and configured to sense the heart rate of the care receiver based on the bioelectricity generated by muscle contraction. It is to be understood that the aforementioned types of the physiological signal sensor 132 are provided for an exemplary purpose only, and the type and quantity of the physiological signal sensor 132 are not limited in the present invention.

In the present embodiment, the signal processing module 133 converts the impedance value between the wires 122 sensed by the impedance sensor 131 and the physiological signal sensed by the physiological signal sensor 132 into the notification signal. The wireless signal transmitter 136 of the transceiver assembly 130a then transmits the notification signal to the monitoring module 200. The monitoring module 200 then receives the notification signal through the wireless signal transmitter 210 thereof. Finally, the signal processing module 220 of the monitoring module 200 analyzes the notification signal, such as analyzing the time-dependent impedance values and changes sensed by the impedance sensor 131 to determine the physiological behaviors (such as urination, excretion or sweating) and analyzing the physiological signals sensed by the physiological signal sensor 132 to determine the physiological conditions (such as heart rate, respiration rate and skin temperature) of the care receiver.

In the present embodiment, the transceiver assembly 130a includes the impedance sensor 131 and the physiological signal sensor 132. Therefore, the transceiver assembly 130a is able to monitor not only the physiological behaviors (such as urination, excretion, or sweating) but also the physiological conditions (such as heart rate, respiration rate and skin temperature) of the care receiver. As a result, through the physiological monitoring device of the present embodiment that is capable of monitoring the physiological behaviors and the physiological conditions at the same time, the health condition of the care receiver can be monitored and predicted in real time and therefore burden of the caregivers is reduced. In addition, because the smart nursing consumable 100 is disposed close to the care receiver's skin, the transceiver assembly 130a would also be close to the care receiver's skin once the transceiver assembly 130a is connected to the smart nursing consumable 100. Therefore, measurement accuracy of the physiological signals (such as heart rate, respiration rate and skin temperature) of the care receiver is improved.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A smart nursing consumable, comprising:
   an absorbent body, comprising a water-absorbing layer and a water draining layer disposed above the water-absorbing layer; and
   a sensor module, disposed on the water draining layer and comprising a plurality of wires, a first porous sheet, a second porous sheet and a conductive pad, wherein the wires are disposed between the first porous sheet and the second porous sheet, the first porous sheet is disposed adjacent to the water-absorbing layer, and the conductive pad is connected to the wires through pores of the second porous sheet.

2. The smart nursing consumable according to claim 1, wherein a material of the conductive pad is selected from at least one element in a group consisting of conductive plastic gum, conductive gel, conductive plastic, conductive ink, conductive paint and carbon film.

3. The smart nursing consumable according to claim 1, wherein the smart nursing consumable comprises smart nursing pants, a smart diaper, a smart nursing pad, a smart sanitary napkin or smart gauze.

4. A physiological monitoring device, comprising:
   the smart nursing consumable according to claim 1;
   a transceiver assembly, removably coupled to the smart nursing consumable, the transceiver assembly comprising:
      an impedance sensor, electrically connected to the wires and configured to sense an impedance value between the wires so as to obtain a plurality of time-dependent impedance values and a time-dependent impedance change; and
      a signal processing module, electrically connected to the impedance sensor and configured to convert the time-dependent impedance values and the time-dependent impedance change sensed by the impedance sensor into a notification signal, wherein the notification signal indicates active conditions of the smart nursing consumable; and
   a monitoring module, configured to receive the notification signal provided by the transceiver assembly.

5. The physiological monitoring device according to claim 4, wherein the transceiver assembly further comprises a physiological signal sensor, the physiological signal sensor is electrically connected to the signal processing module and configured to sense a physiological signal of a care receiver.

6. The physiological monitoring device according to claim 5, wherein the physiological signal sensor comprises an acceleration sensor, the acceleration sensor is disposed close to the smart nursing consumable and configured to sense at least one of a heart rate and a respiration rate of the care receiver.

7. The physiological monitoring device according to claim 5, wherein the physiological signal sensor comprises a thermal resistor, the thermal resistor is disposed close to the smart nursing consumable and configured to sense a skin temperature of the care receiver.

8. The physiological monitoring device according to claim 7, wherein the skin temperature increases with a severity of a wound infection of the care receiver.

9. The physiological monitoring device according to claim 5, wherein the physiological signal sensor comprises a bioelectric sensor, the bioelectric sensor is disposed close to the smart nursing consumable and configured to sense a heart rate of the care receiver.

10. The physiological monitoring device according to claim 4, wherein the absorbent body has a diaper-like shape, the transceiver assembly further comprises a clamp body, and the clamp body is configured to clamp a belt of the absorbent body.

11. The physiological monitoring device according to claim 4, wherein the transceiver assembly further comprises a wireless signal transmitter, the wireless signal transmitter is electrically connected to the signal processing module and configured to transmit the notification signal.

12. The physiological monitoring device according to claim 4, wherein the monitoring module comprises a reminder element.

13. The physiological monitoring device according to claim 4, wherein the monitoring module comprises a monitoring data transfer element.

* * * * *